United States Patent
Sakazume et al.

(10) Patent No.: US 8,628,720 B2
(45) Date of Patent: Jan. 14, 2014

(54) AUTOMATIC ANALYZER

(75) Inventors: Taku Sakazume, Hitachinaka (JP); Kantaro Suzuki, Mito (JP)

(73) Assignee: Hitachi High-Technologies Corporation, Tokyo (JP)

( * ) Notice: Subject to any disclaimer, the term of this patent is extended or adjusted under 35 U.S.C. 154(b) by 98 days.

(21) Appl. No.: 13/145,424

(22) PCT Filed: Jan. 13, 2010

(86) PCT No.: PCT/JP2010/000117
§ 371 (c)(1),
(2), (4) Date: Sep. 9, 2011

(87) PCT Pub. No.: WO2010/087108
PCT Pub. Date: Aug. 5, 2010

(65) Prior Publication Data
US 2012/0114525 A1    May 10, 2012

(30) Foreign Application Priority Data

Jan. 30, 2009 (JP) .................................. 2009-018942

(51) Int. Cl.
*G01N 33/00* (2006.01)

(52) U.S. Cl.
USPC .................. 422/52; 422/400; 422/82.05

(58) Field of Classification Search
USPC ............................ 422/52, 400, 82.05
See application file for complete search history.

(56) References Cited

U.S. PATENT DOCUMENTS

| 2002/0099511 A1 | 7/2002 | Matsushita et al. |
| 2003/0045716 A1 | 3/2003 | Natrajan et al. |

FOREIGN PATENT DOCUMENTS

| JP | 59-125043 A | 7/1984 |
| JP | 6-50894 A | 2/1994 |
| JP | 11-507726 A | 7/1999 |
| JP | 2001-100340 A | 4/2001 |
| JP | 2002-195948 A | 7/2002 |
| JP | 2003-50204 A | 2/2003 |
| JP | 2004-205508 A | 7/2004 |
| JP | 2007-85804 A | 4/2007 |
| JP | 2008-89450 A | 4/2008 |

OTHER PUBLICATIONS

Translation document for JP 2004-205508 claims.*
Translation document for JP 2004-205508 description.*
Hamamatsu Photonics, How to Used Photomultiplier Tubes, Second Edition, 2007.

* cited by examiner

*Primary Examiner* — Sam P Siefke (74) *Attorney, Agent, or Firm* — Mattingly & Malur, PC (57) ABSTRACT

Photomultiplier tubes differ in performance between individual products, and deteriorate over time. To appropriately use a nonlinear calibration curve, it is desirable that changes in signal level be strictly equalized. This invention includes means for, prior to sensitivity adjustment of a photomultiplier tube by application of high voltages, measuring a same sample under a plurality of high-voltage conditions, determining, from linear relationships between logarithms of each high voltage and those of signal levels, an optimal voltage for a measuring operation of predetermined order of execution in the plurality of measuring operations, and recording identification information for identifying each linear relationship; the invention assessing a healthiness level of the photomultiplier tube by assessing the linear relationship.

9 Claims, 5 Drawing Sheets

AUTOMATIC ANALYZER

TECHNICAL FIELD

The present invention relates to an automatic analyzer for analyzing biologically derived samples, and more particularly, to an automatic analyzer using a photomultiplier tube.

BACKGROUND ART

The heterogeneous immunoassay exists as a method for assaying hormones and other chemical constituents contained in very small quantities in blood and the like. In this method, a luminescent reaction, such as a chemiluminescence as described in Patent Document 1 or an enzyme-based electrochemiluminescence as described in Patent Document 2, is detected by a photomultiplier tube. A calibration technique for a photomultiplier tube is disclosed in Patent Document 3. In this technique, a spectrophotometer has a plurality of calibration curves associated with a plurality of detection sensitivities of a photomultiplier tube.

In addition, Patent Document 4 discloses a method of signal processing in a detection instrument using a photomultiplier tube in the chemiluminescent method, and Patent Document 5 discloses a method of sensitivity adjustment in a photomultiplier tube.

Quantitative measurements on the concentrations of the chemical substances contained in blood, urine, and other body fluids, such as proteins, lipids, sugar, ions and their constituents, are performed at clinical sites. The clinical examination apparatus includes an automatic analyzer where preparation of an aliquot of a body fluid or other liquid sample; mixture of the aliquot with a reagent; and measurement of the change of a substance contained in the reagent as a result of reaction with the reagent are performed. Such an automatic analyzer is configured so that the processes required for analysis, including mixture of a sample with a reagent and reaction at a constant temperature, are successively performed at given times. Automatic analyzers are configured to undertake mixing the sample and reagents required for analysis, causing reactions at a constant temperature, and various other processes, one after another, within a required time.

Of these automatic analyzers, apparatus that measure the minute quantities of hormones and other chemical constituents contained in blood or other substances employ a heterogeneous immunoassay method, in which the luminescence obtained is measured using a highly sensitive element such as a photomultiplier tube.

If a substance to be subjected to high-sensitivity analysis is very small in biogenic content, the concentration itself of the substance has insignificant effects upon constancy, such that the concentration is measured in a significantly wide range. The content of blood thyroid-stimulating hormone, for example, is required to be detected and measured in a range from 0.001 µIU/ml to 100 µIU/ml, this spread between both being as much as 100,000 times.

At the same time, since the objective of the data obtained varies from one concentration region to another, predetermined specific resolution is demanded for an infinitesimal range, a normal range, and a high-concentration range each.

Reagents with varying sensitivity to one specific substance to be measured are often supplied for those measurement items. However, supplying a special reagent for each of analytical items with a very low frequency of analysis involves a heavy economical burden. Therefore, detectors and reaction systems applicable to higher sensitivity (a range of infinitesimal quantity) have been provided, and for higher-concentration measurement, a necessary reagent has been diluted from several times to several hundreds of times, to increase substantial detection sensitivity.

However, if a substance whose content stays in an infinitesimal range and whose concentration equilibrium has been reached in the presence of other constituents in the serum is diluted with a normal saline solution, signal levels may not change according to the particular dilution rate. In addition, an immunoassay, generally called the sandwich method, is used for a substance whose content lies in a low-concentration region, in particular. In the sandwich method, the linearity of output signals is lost since noise such as the luminescence in the reagent constituents is augmented in comparison with the signals derived from the substance to be measured.

In a high-concentration range, in contrast, the relative quantitative ratio of the reagent constituents to the constituents in the sample decreases, which results in insufficient progress of reactions. In this case, the linearity of output signals is also lost.

Quantitative determination of concentrations in a wider range, therefore, may conveniently use nonlinear calibration curves. The calibration curves used include a spline curve, a curve created by combining an exponent and a logarithm, a polynomial calibration curve created by combining a plurality of lines, and more. A calibration curve that becomes a prototype, that is, a master curve is created using at least five points. The calibration curve is often transformed during actual measurement. One method of transforming the calibration curve uses two typical points to shift the curve in parallel with respect to the position of the minimum signal level. Another method is by dimensionally changing the range of the minimum and maximum signal levels in telescopic form to fit the positions of both signal levels. Input data (X-axis data) of the calibration curve denotes the signal levels detected by the detection unit of the system and calculated by the arithmetic unit of the system, and output data (Y-axis data) represents the concentration of the substance measured.

To conduct such transformation appropriately, the signal levels that become the input of the calibration curve need to stay in a fixed range. For this reason, the entire detection system including the detector is adjusted using a pseudo sample that is prepared using weight or capacity beforehand outside the measuring device. Prior to the adjustment of the detection system, desired signal levels with respect to the pseudo sample are assigned and then the desired signal levels are adjusted by controlling the high voltage applied to the detector to obtain the desired signal levels.

The photomultiplier tube commonly used for such high-sensitivity analysis is one kind of vacuum tube. Details are shown in Non-Patent Document 1. A high voltage of about 1,000 V is applied between a cathode that receives light inside the vacuum tube, and an anode that extracts a final signal. The light with which the cathode surface of the photomultiplier tube has been irradiated is multiplied by utilizing the differential potential between both electrodes to obtain an amplification effect of nearly $10^6$.

PRIOR ART LITERATURE

Patent Documents

Patent Document 1: JP-2003-50204-A
Patent Document 2: JP-11-507726-A
Patent Document 3: JP-59-125043-A
Patent Document 4: JP-2007-85804-A
Patent Document 5: JP-2001-100340-A Non-Patent Document Non-Patent Document 1: HAMAMATSU PHOTONICS, "How to Use Photomultiplier Tubes", Second Edition

SUMMARY OF THE INVENTION

Problems to be Solved by the Invention

Because of their characteristics, photomultiplier tubes differ in sensitivity between the products to which they are applied. At high voltages of the photomultiplier tubes, adjustment values may change over an 800 to 1000 V range, depending on the detector. Additionally, deterioration with time is shown in Non-Patent Document 2. When exposed to strong light or repeatedly used for measurement, photomultiplier tubes decrease in sensitivity (this event is called deterioration or fatigue).

Adjusting the sensitivity of a photomultiplier tube utilizes the fact that as shown in Patent Document 3, a certain relationship exists between a logarithm of the high voltage applied to the photomultiplier tube, and a logarithm of the signal level obtained during analysis of the same item. According to Patent Document 2, a light-storing material for radiation measurement is used as a luminous element that becomes a reference. Patent Document 2, however, does not describe how to provide for the amount of light to be emitted. The numerical value is concretely given to the expression, it is difficult to estimate what form of expression is appropriate when a different light source is used.

In addition, when a system using a photomultiplier tube in a detector is actually configured, a failure in the photomultiplier tube is difficult to accurately predict, since steps up to detection includes a plurality of elements.

Repeating overall system checks at approximate cycles from six months to twelve months would be probable. Whether to replace the photomultiplier tube during such checks has been unpredictable, except in case of the photomultiplier tube being unadjustable during the checks. Because of that, some users have requested a maintenance service by saying that one day, when the device was started, the device did not provide a predetermined signal level and suddenly became inoperative. The photomultiplier tube has been consequently replaced as integral part of the maintenance service. At clinical sites, where urgent testing is likely to be requested, it has been necessary to appropriately understand and assess the performance of the photomultiplier tube for preventive maintenance purposes.

Furthermore, the deterioration of the photomultiplier tube is estimated to progress according to the sum of the amount of light received. In the process steps that the analyzer system executes, exposure to the amount of light exceeding that developed during measurement can occur during other operations. In an extreme case, the detection unit of the photomultiplier tube could include an optical shutter, but this is less likely to be realized, for costs would correspondingly increase.

An object of the present invention is to provide an automatic analyzer that uses a photomultiplier tube, the automatic analyzer being provided with an optimal adjusting mechanism for the photomultiplier tube. Another object of the invention is to provide an automatic analyzer including a mechanism to detect deterioration of a photomultiplier tube.

Means for Solving the Problems

One sample is assayed using a plurality of different high-voltage parameters, and signal levels corresponding to each high-voltage parameter are measured. A gradient is calculated from a line obtained by plotting logarithmic values of the applied high voltage on an X-axis, and those of each measured signal level on a Y-axis. Next, it is verified that the photomultiplier tube is in a healthy condition. If the photomultiplier tube is unhealthy, a warning that includes replacement is displayed from a system.

Another method is by making luminous a pseudo sample prepared outside the system, then using a plurality of high-voltage parameters to obtain signal levels from the sample, and calculating a gradient of a line appearing between a logarithm of each high voltage and that of each signal level. A high-voltage value that is appropriate for obtaining the amount of light expected and is of a minimal deviation from the line is derived from the data calculated above. Additionally, at least one of the gradient and an intercept is used to verify that the photomultiplier tube is in a healthy condition. If the photomultiplier tube is unhealthy, a warning that includes replacement is displayed from the system.

With regard to a time during which the photomultiplier tube is not involved in detection, the high voltage applied to the photomultiplier tube is reduced to suppress an amplification process occurring inside the photomultiplier tube, and hence to suppress deterioration of the photomultiplier tube.

Effects of the Invention

More economical system calibration and monitoring are accomplished by assaying the same sample using a plurality of parameters during high-voltage adjustment.

MODE FOR CARRYING OUT THE INVENTION

Hereinafter, embodiments of the present invention will be described with reference to the accompanying drawings.

Embodiment 1

An analyzer system according to an embodiment of the present invention relating to chemical analysis which uses a photomultiplier tube as a detector and an acridinium-ester-based chemiluminescent method as a detection method is first described below.

Figure 1:
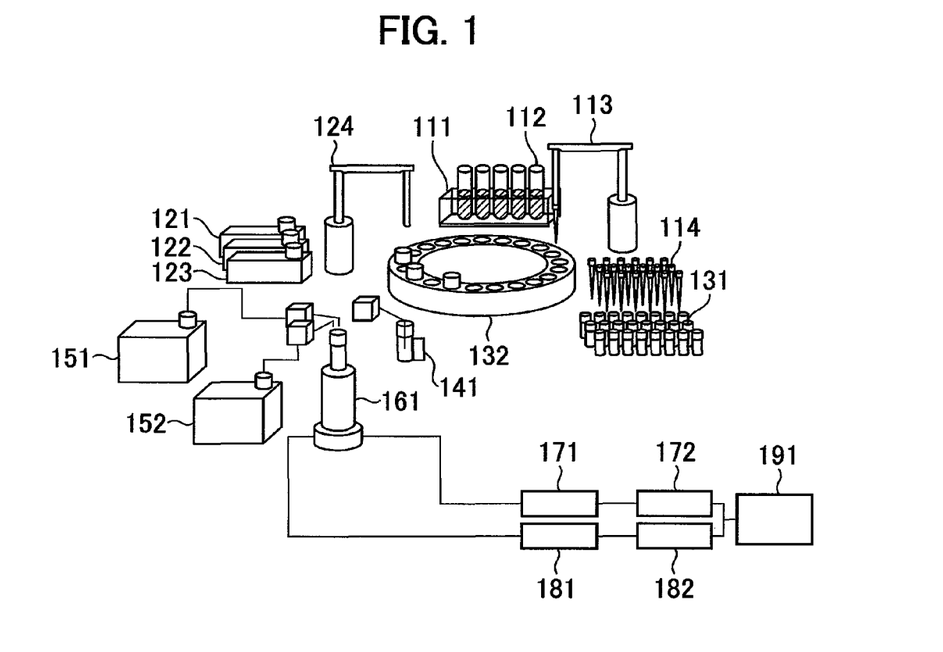
FIG. 1 is a schematic explanatory diagram of an analyzer system using a chemiluminescent method.

FIG. 1 is a schematic of the system. The system uses a sampling mechanism 113 to suction the contents of sample containers 112 placed in racks 111. Each rack 111 is sequentially positioned close to the sampling mechanism 113. Neither a control section that controls various mechanisms cooperatively, nor part of a mechanism for moving reaction vessels 131 as well as sampling tips 114 is shown in FIG. 1. One reaction vessel 131 is set up in place on a reaction transport mechanism 132 having a function of controlling temperature, and then reagents 121 and 122 are dispensed into the reaction vessel 131 by a reagent dispensing mechanism 124. After this, the sampling mechanism 113 dispenses a predetermined amount of sample into the reaction vessel on the reaction vessel transport mechanism 132, and the reagents and sample in the reaction vessel are next mixed by suctioning and/or discharging. After this, the reaction vessel containing the mixture is retained on the reaction vessel transport mechanism 132 for a reaction time of about nine minutes, for example, to cause a reaction. Additionally, the reagent dispensing mechanism 124 dispenses a predetermined amount of suspension that contains magnetic particles, from a reagent container 123 into the reaction vessel, to cause a further reaction for about nine more minutes. A magnetic separator 141 separates the contents of this reaction vessel into the magnetic particles and a supernatant, and then moves the reaction vessel to a detection unit. The detection unit having a function that injects an acid hydrogen peroxide solution 151 and a sodium hydroxide solution 152 into the reaction vessel causes a chemiluminescent reaction near a photomultiplier tube 161. Upon a high voltage being supplied to the photomultiplier tube from a high-voltage generator 171 via a D/A converter 172 connected to a main control device 191, an electric current signal that is output according to the amount of light is logarithmically converted by a logarithmic converter 181. At the same time, the signal is converted into a voltage signal by an A/D converter 182, which is then delivered to a main control device 191.

Figure 2:
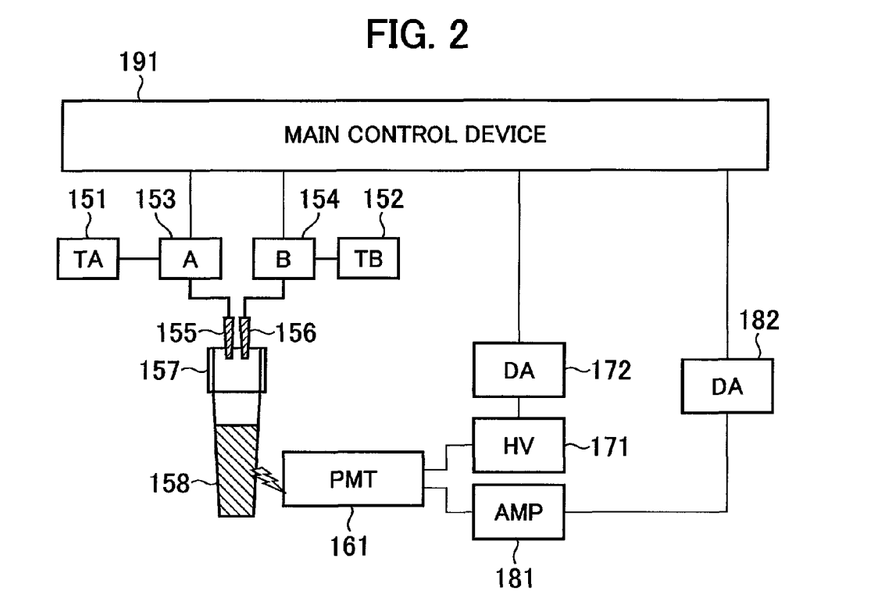
FIG. 2 is an explanatory diagram of a detection unit of the analyzer system using a chemiluminescent method.

FIG. 2 shows details of the chemiluminescent process. The main control device 191 operates various function blocks cooperatively at predetermined timing. The main control device 191 first activates a pump 153 to supply acid hydrogen peroxide solution A (hereinafter referred to A) to nozzle A 155. Next, discharge solution A into a reaction vessel 157 that internally holds magnetic particles or a solution containing an acridinium ester to mix solution A and the magnetic particles or the solution containing the acridinium ester. The main control device 191 additionally activates a pump 154 to supply sodium hydroxide solution B (hereinafter referred to B) to a liquid 158 made by the mixing operation, through nozzle B 156, then causes emission of light. Part of the emitted light is converted into an electric current by the photomultiplier tube 161 and then transmitted to the main control device 191 via an A/D converter 182.

Figure 3:
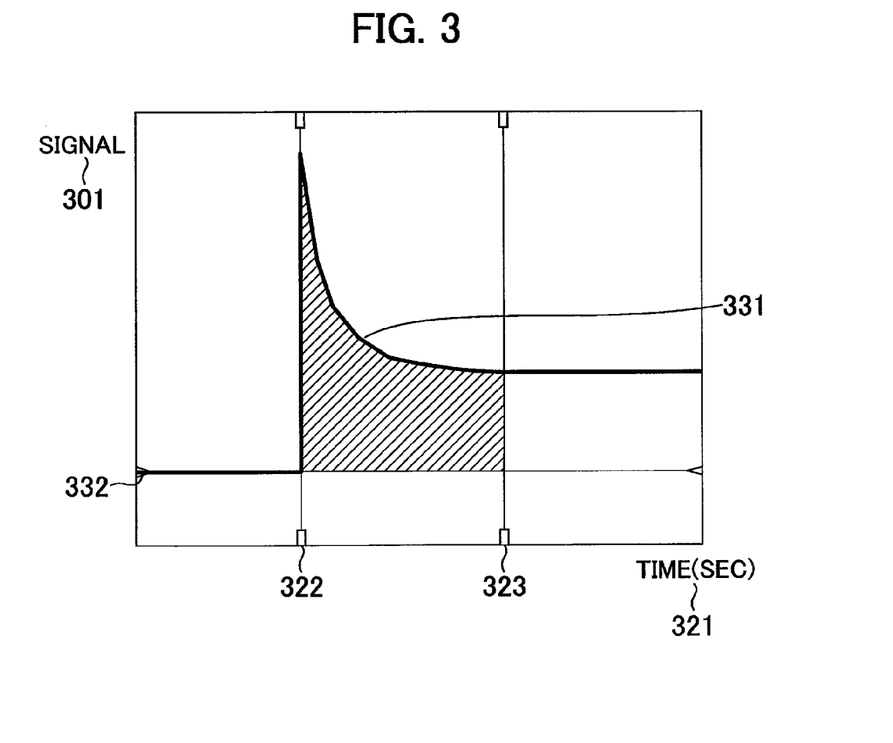
FIG. 3 is a diagram that shows a method of integration from an elapsed time of light emission in the chemiluminescent method.

FIG. 3 is a process diagram of data processing. Time (seconds) 321 is plotted on an X-axis, and a signal level 301 on a Y-axis. The signal level is a measured photocurrent signal, so that a time interval that becomes its unit is A (amperes) or the number of electrons (pieces). An output signal level 331 indicates that after the emission of the light was started from timing 322 at which a neutralization reaction by the sodium hydroxide solution passed a point of neutralization, the quantity of the light reaches a peak and then gently decreases. The emission process depends on a behavior, concentration, and mixing speed of the chemical substance mixture subjected to the reaction. After that, predetermined range from nearly 0.4 to 1.0 second from sodium hydroxide solution injection timing 322 is integrated, except for a pre-injection emission level 332 of the light. The value that has thus been obtained is taken as an emission level. A dimension of the emission level is equivalent to the quantity of charge or the number of photons. Hereinafter, the emission level is expressed in terms of count.

Figure 4:
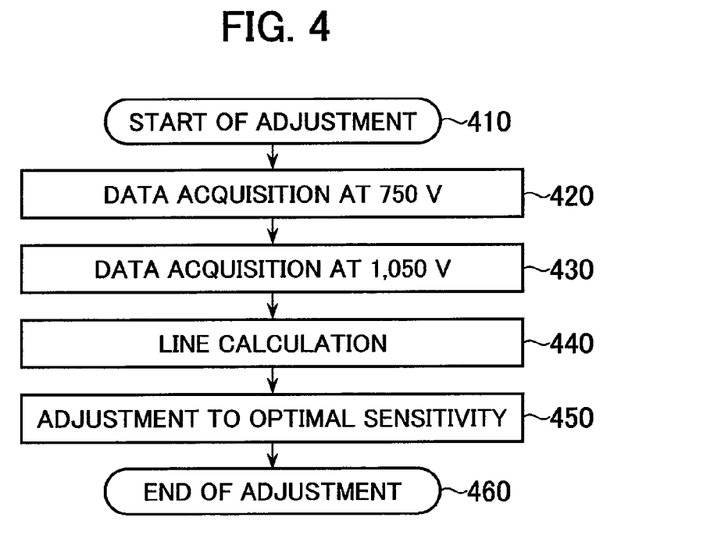
FIG. 4 is a flow diagram of photomultiplier tube sensitivity adjustment.
Figure 5:
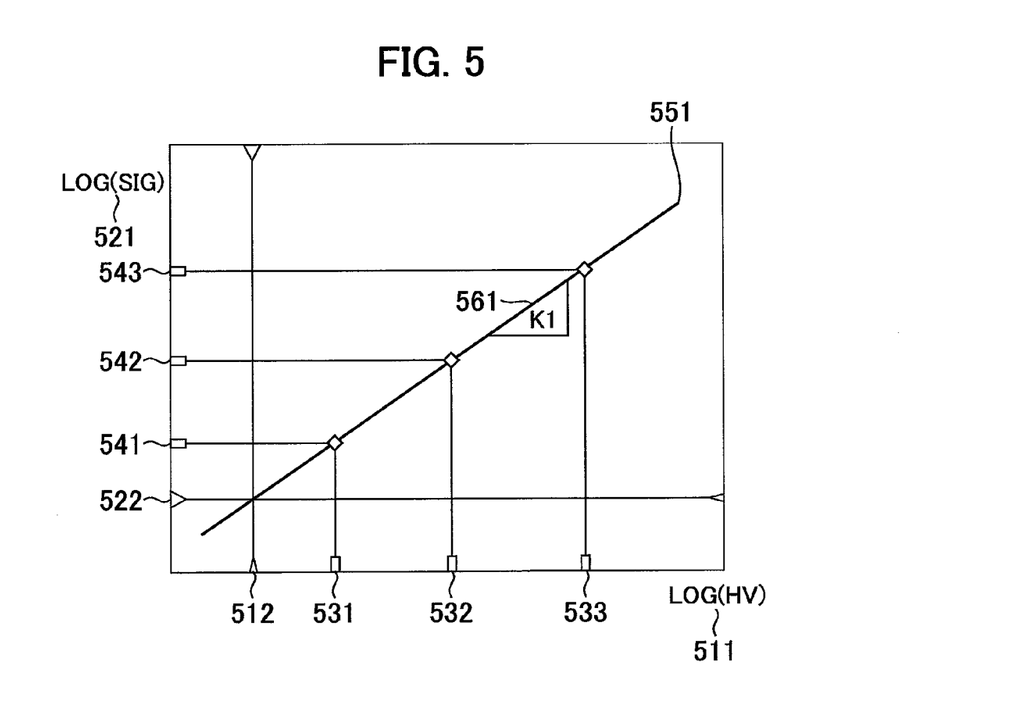
FIG. 5 is a diagram that shows automatic sensitivity adjustment method of the photomultiplier tube.

The following describes a method of adjusting the sensitivity of the PMT with respect to the emission level thus calculated. The description assumes that a solution formed by dissolving a required amount, for example 10 pg/L, of luminous compound, for example an acridinium ester, of a known concentration, is prepared prior to the adjustment of the photomultiplier tube. The description also assumes that the emission level obtained from this solution is next conditioned to 100,000 counts, for example. One advantage from using the solution is that traceability can be ensured by using a gravimetric method. In chemical analysis, therefore, the weight in a definite volume is most commonly used, but in actual applications, it may be rather appropriate to control the value in terms of weight concentration, as in 10 pg/kg. The above definite solution being quantitatively determined using the sample dispensing device 113 or quantified as a reagent by use of the reagent dispensing device 124, is dispensed into the reaction vessel 157 and then made luminous by using a required method, thereby to obtain a signal. FIG. 4 shows a process flow of the adjustment. FIG. 4 envisages an approximate PMT adjustment range from 800 V to 1,000 V. Upon execution of a starting step 410 of the adjustment, measurement of signal levels is started using 15 samples, for example. First, the signal levels of five of these samples are measured under a high-voltage condition of 750 V. Let this voltage value be equivalent to a sensitivity level slightly below a lower limit of a practical range. The signal levels of next five of the 5 samples are measured at 1,050 V. Let 1,050 V be equivalent to a sensitivity level slightly above an upper limit of the practical range. A chart shown in FIG. 5 is created from measurement results, and after the charting, the high voltage and the corresponding signal level are plotted on the X-axis 511 and the Y-axis 521, respectively, in logarithmic form. An X-coordinate of a point obtained by the measurement at 750 V is shown as 531, and a Y-coordinate of the point, as 541. In FIG. 5, averaged values are used for simplicity of representation, but respective subjects of measurement may instead be displayed as scatter diagrams. Next, the point where the measurement at 1,050 V was conducted is plotted as an X-coordinate 533, Y-coordinate 543. A regression line 551 is derived from the two points described above. Simply, it follows:

Gradient 561=(Log(emission level at 1050 V)−Log (emission level at 750 V))/(Log(1050V)−Log (750V)).

This gradient may be determined by conducting measurements at a plurality of points at both ends of 750 V and 1,050 V and between the ends, and deriving a line using the least squares method. Photomultiplier tubes exhibit high linearity with respect to voltage. One possible approach if repeatedly deriving the relationship between the same high voltage and the emission level is by, for example, calculating those standard deviations and then if the count of variations that is obtained is equal to or more than 1%, repeating the measurement itself from the beginning.

A high voltage 532 for an emission level 542 which is to be adjusted can be set for the line derived above.

Furthermore, N=5 is specified and measurement is repeated with the high-voltage setting 532. For example, it is verified that an error in the emission level is 0.5% or less. It is also verified that high repeatability can be gained and that, for example, the variations count is less than 1%. Upon completion of the verification of these facts, the adjustment sequence is completed.

Embodiment 2

A method of assessing changes in performance of a photomultiplier tube with time and notifying a warning is described below as embodiment 2 of the present invention. During photomultiplier tube servicing in the presence of fluorescent lamps, no problems are considered to occur unless a high voltage is applied. Even when the high voltage is not applied, however, if exposed to daily interior lighting or other light rays including ultraviolet, photomultiplier tubes suffer the deterioration that causes loss of the photocathode of an orange color, for example, and/or loss of the electrical interconnects of metallic luster that are used for connection to the photocathode. That is, although distinct deterioration due to a brief time of exposure lies in a range of errors in macroscopic perspective or in terms of a signal level, exposure to light rays is estimated to cause deterioration. Accordingly, performance is considered to deteriorate progressively if the photomultiplier tube is exposed to during the manufacture or maintenance of the system or strong rays during measurement. Repeated measurement over an extended period of time occasionally reduces signal levels. This, however, is due to interactions between a unique nature and exposure history of the particular photomultiplier tube product, such that causes of deterioration cannot be easily estimated.

Figure 6:
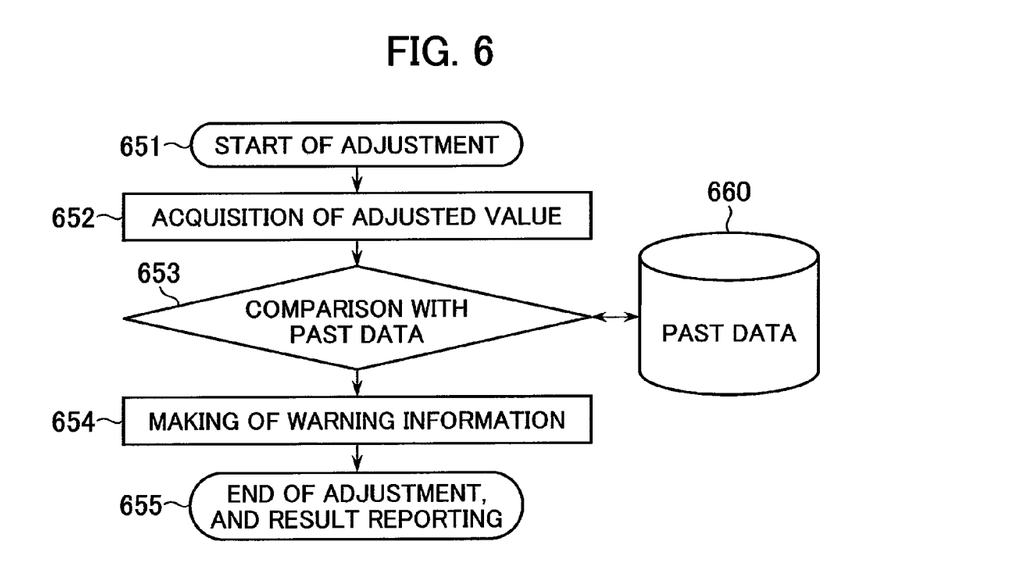
FIG. 6 is a flow diagram of photomultiplier tube sensitivity determination.
Figure 7:
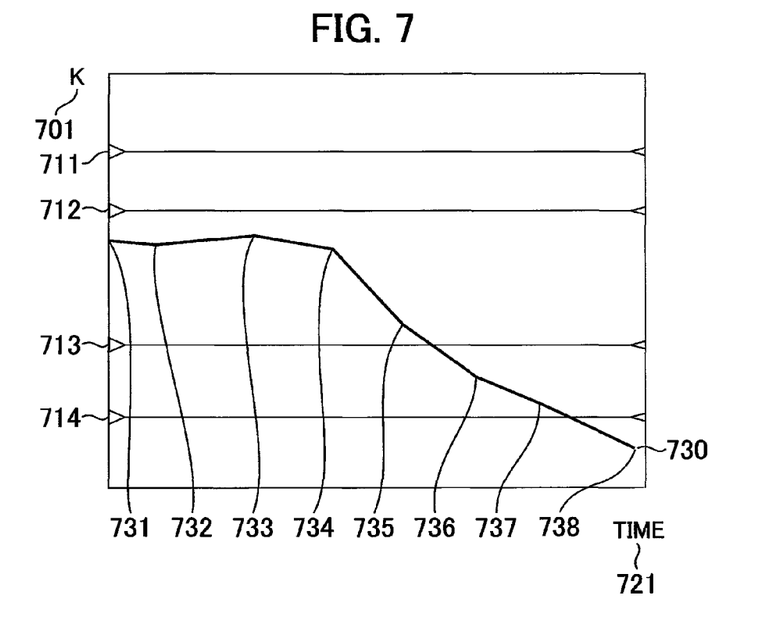
FIG. 7 is a diagram that shows changes in the photomultiplier tube sensitivity as plotted with an elapse of time.

For these reasons, during the adjustment of the photomultiplier tube, a sequence shown in FIG. 6 is used to compare present data with past data and make warning information. Upon execution of a starting step 651 of the adjustment, adjusted values are obtained in step 652 using such a method described in the embodiment 1. Next, the comparison 653 with the past data 660 takes place, which is then followed by the making of warning information 654 from comparison results, and further followed by adjustment result reporting 655. The warning may be displayed on an operating screen intended for the adjustment. As shown in FIG. 7, a value that indicates time-varying changes such as time, measurement frequency of light, maintenance frequency, or the like, is plotted on an X-axis 721, and a gradient is plotted on a Y-axis 701 using reference numbers 731 to 738 to denote the maintenance frequency. This enables the system to prompt replacement by determining whether the gradient ranges between an upper limit 712 and lower limit 713 of a caution level or between an upper limit 711 and lower limit 714 of a warning level. For example, if the count decreases below the lower limit 713 of the caution level and reaches the warning level 714, replacement is desirably scheduled in advance. Frequency of use of such an automatic analyzer system varies from product to product, replacement timing can likewise be prescheduled by collecting the information of interest remotely at a Service Center.

Embodiment 3

Figure 8:
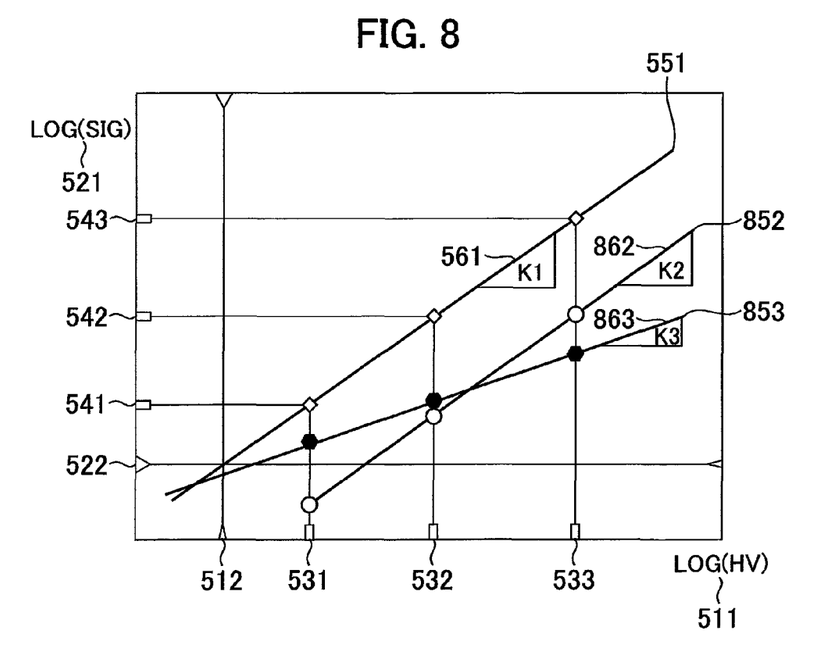
FIG. 8 is an explanatory diagram of changes in the sensitivity of the photomultiplier tube.

A method of assessing performance of a photomultiplier tube during analysis of a precision control sample or of a standard sample used as a calibration sample in clinical tests shown in FIG. 8. The pseudo sample for calibration, described in the embodiment, is generally used during analyzer installation or after part replacement, and is not used for operational purposes in routine clinical tests. Both interpretation of assessment result data and troubleshooting require expertise. Briefly, the pseudo sample is intended primarily for the suppliers or vendors of the system who profess servicing, or for users who exclusively use the system. In contrast, standard solutions and precision control samples, provided for TSH or other subjects of analysis that are used for actual measurement with the system, are samples intended for daily use by persons who conduct clinical tests.

The relationship between a signal level and a concentration is in general set for standard solutions and precision control samples. In general, standard samples are supplied together with clinical reagents from suppliers of the clinical reagents. For the high-sensitivity immunoanalytical method, in particular, that use a highly sensitive element and involve the reagents whose product quality usually varies from lot to lot, standard solutions are supplied from suppliers who supply clinical reagents to the system. Therefore, when two kinds of standard solutions, for example one kind for low concentrations and the other kind for high concentrations, are to be supplied, the suppliers need to have, during the system manufacturing phase, a prior knowledge of what signal levels the respective kinds of standard solutions will exhibit.

Precision control samples are samples for which an allowable concentration range is presented beforehand. If the apparatus is appropriately pre-calibrated using a standard sample, levels of the signals output from the apparatus can be estimated. During use of a precision control sample and a standard sample, when the same sample is repeatedly measured a plurality of times using a photomultiplier tube placed under different high-voltage conditions, this enables an operator to know a in what condition the photomultiplier tube is, by obtaining a gradient of a logarithm of the signal level with respect to that of the high voltage being exerted upon the photomultiplier tube. These samples are most commonly supplied in sufficient quantities of, for example, 2 mL for one measuring operation. Therefore, it is very efficient for economic reasons to know the state of the photomultiplier tube using residual samples after calibration. For example, in a system capable of measuring signal levels equivalent to light-emission levels from about 500 to 5,000,000 counts with high linearity, high voltages to be applied to the photomultiplier tube are desirably determined by assuming signal levels from about 100,000 to 1,000,000 counts in terms of emission level, as presented in the embodiment 1. If the sample is to be used to monitor a state of the photomultiplier tube, items that yield signal levels from about 10,000 to 1,000,000 counts, retain reagent stability, and are excellent in simultaneous repeatability, may be selected. In general, during high-sensitivity analysis, the quantity of TSH (thyroid-stimulating hormone) is commonly measured using sandwich method as high-sensitivity immunoanalytical method. If a precision control sample that exhibits a healthy persons' average concentration ranging approximately between 0.5 μIU/ml and 4.0 μIU/ml, appropriate signal levels from nearly 5,000 to 100,000 counts are estimated to be obtainable.

Concentrations are desirably measured at high voltages, for example, 750 V and 1,050 V, in accordance with substantially the same sequence as that indicated in the flow diagram of FIG. 4. However, using a high voltage that only yields too low an emission level may result in signal loss. Care is therefore required so as not to use data such as emission levels below 1,000 counts.

For comparison purposes with respect to the regression line 551 obtained under initial high-voltage loading shown in FIG. 5, FIG. 8 shows a regression line 852 obtained when a sample of a low emission level was analyzed under a maintained state of the photomultiplier tube in substantially the same system configuration as that shown in FIG. 5.

As shown in FIG. 8, no dependence upon the emission level is observed. Nor is observed an appreciably significant change in a gradient of the regression line 551 indicative of changes in signal level 521 with respect to the high photomultiplier tube voltage 551. For these reasons, during analyzer installation and/or maintenance, when the photomultiplier tube is adjusted, the sample of the low emission level forms the line 852 including a gradient <K2> 862. The gradient <K2> 862 takes a form different from that of the gradient <K1> 561 in intercept size, and shifted in parallel with respect to the gradient <K1> 561 of the line 551. However, even for a photomultiplier tube that exhibits signal levels equivalent to those of an adjusting sample, decreases in sensitivity result in formation of a line similar to a line 853 having a gradient <K3> 863 reduced in intercept size. The change in intercept size is due to a change in the amount of light. If the gradient remains invariant and only the intercept size changes between samples of the same kind, therefore, this implies that a problem exists between the luminous side and the photomultiplier tube. Since the inside of the photomultiplier tube itself also has a plurality of factors that cause deterioration, causes of the change in intercept size are estimated not to be uniform.

Figure 9:
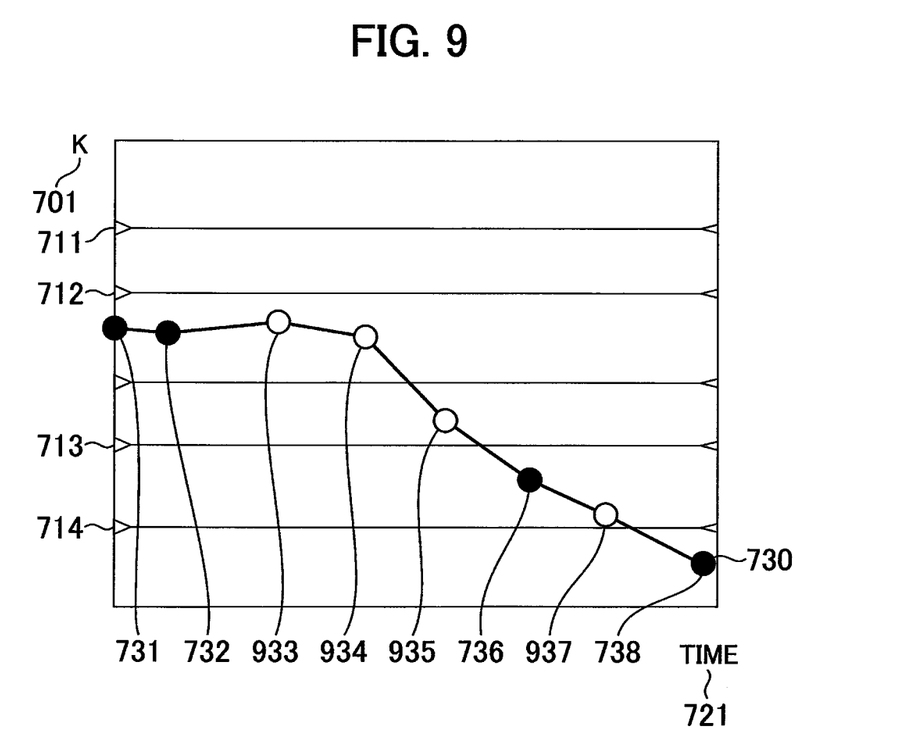
FIG. 9 is a diagram that shows changes in the photomultiplier tube sensitivity as measured using a calibration sample and plotted.

It pays attention to the gradient, and details that plotted the gradient at the time of passing are shown in FIG. 9.

Execution results 933, 934, 935 on monthly photometry with calibration samples, for example, are plotted against a value 731 obtained during system manufacturing, and a value 732 obtained during analyzer installation at a user site. A value 736 obtained during verification in any maintenance operations, and execution results 937 on following calibration are both present, so the fact that the photomultiplier tube is in a state that requires replacement can be verified. It can be judged, therefore, that before results estimated to be obtained in next verification 738 are presented, the replacement should be executed. For more effective monitoring, a measurement repetition count, that is, a total amount of light exposure that the photomultiplier tube has undergone, can be plotted on an X-axis, and a gain, on a Y-axis. In addition, a warning can be displayed if the gain decreases by a certain level or more with respect to an increase in the total exposure rate.

In the present method, samples in routine use can thus be used to monitor for an unusual state of the system, to operate the system in a healthy condition, and to prevent occurrence of trouble. In addition, these maintenance operations can be performed without depending upon the concentration or emission level of the sample. Even when an LED or a lamp is used as a standard light source, the present method enables gain levels to be calculated from measurement results obtained using different high voltages, and performance to be assessed similarly. In such a case, it suffices if the standard light source provides a fixed emission level between measurement operations, and susceptibility of operational stability to extended periods of operation is minimized.

DESCRIPTION OF REFERENCE NUMERALS

111 Rack
112 Sample container
113 Sampling mechanism
114 Sampling tip
121 Reagent dispensing mechanism
122 Reagent
123 Reagent container
131, 157 Reaction vessel
132 Reaction vessel transport mechanism
141 Magnetic separator
151 Acid hydrogen peroxide solution
152 Sodium hydroxide solution
153 Pump that supplies acid hydrogen peroxide solution A (hereinafter A)
154 Pump that supplies sodium hydroxide solution B (hereinafter B)
155 Nozzle A
156 Nozzle B
158 Liquid mixture
161 Photomultiplier tube
171 High-voltage generator
172 D/A converter
181 Logarithmic converter
182 A/D converter
191 Main control device
301 Signal level, Y-axis
321 Time (seconds), X-axis
322 Timing at which a point of neutralization was passed
331 Output signal
332 Pre-injection emission level of light
410, 651 Start of adjustment
511 High voltage, X-axis
521 Signal level, Y-axis
531 X-coordinate of point obtained by measurement at 750 V
532 High voltage with respect to emission level to be adjusted
533 X-coordinate of point obtained by measurement at 1,050 V
541 Y-coordinate of point obtained by measurement at 750 V
542 Emission level to be adjusted
543 Y-coordinate of point obtained by measurement at 1,050 V
561 Gradient <K1> by adjusting sample during system manufacturing
652 Process step of obtaining adjustment data
653 Process step of comparing present data with past data
654 Warning information making step
655 Adjustment result reporting step
660 Storage region for past data
701 X-axis denoting either time, measurement frequency of light, or maintenance frequency, or like
711 Upper limit of warning level
712 Upper limit of caution level
713 Lower limit of caution level
714 Lower limit of warning level
721 Y-axis that denotes value of gradient
731 Value obtained during system manufacturing
732 Value obtained during installation at user site
736 Value obtained during verification in any maintenance operations
738 Result to be assumed during next verification
852 Line of a form different in intercept size and shifted in parallel
853 Line resulting from decrease in sensitivity
862 Gradient <K2> by sample of low emission level
863 Gradient <K3> resulting from decrease in sensitivity
933, 934, 935 Execution results on monthly photometry with calibration samples
937 Execution result on following calibration

The invention claimed is:
1. An automatic analyzer comprising:
a photomultiplier tube as a detector;
a high-voltage generator for generating an applied voltage for driving the photomultiplier tube;
a control circuit for controlling output of the high-voltage generator;

a logarithmic converter for converting the applied voltage to the photomultiplier tube and a measured value of the photomultiplier tube;

an arithmetic unit for determining, from an execution result on the logarithmic conversion of the applied voltage and the measured value, a desired voltage for obtaining a desired sensitivity of the photomultiplier tube, wherein the arithmetic unit includes:
- a storage means for storing measured values under a plurality of applied voltages, with respect to a reagent for assessing sensitivity of the photomultiplier tube;
- a determination means for determining a value of a voltage to be applied to the photomultiplier tube, from relationships between the applied voltages and the measured values, the applied voltages and the measured values being each stored in the storage means; and
- a mechanism that feeds back the determined applied voltage to the control circuit;

a calculator for calculating a rate of change of the measured value to each of the applied voltages as a gain;

a comparison means for comparing threshold levels with the gain calculated by the calculator; and warning means for displaying a warning if the gain is determined to lie outside a range of the threshold levels by the comparing means.

2. The automatic analyzer according to claim 1, further comprising:
means for verifying that at least one of a standard deviation and a measurement error of the measured value in the photomultiplier tube for the applied voltage determined by the determination means lies within a specified value, and wherein if at least one of the standard deviation and the measurement error overstep the specified value, sensitivity of the photomultiplier tube is assessed again.

3. The automatic analyzer according to claim 1, wherein the plurality of applied voltage input to the arithmetic unit are a value greater than a maximum value of a practical voltage applied to the photomultiplier tube, and a value smaller than a minimum value of the practical voltage applied to the photomultiplier tube.

4. The automatic analyzer according to claim 1, wherein the gain calculated by the calculating means is stored chronologically, and the predefined threshold data range is determined from the chronological gain data stored in the means for storing.

5. The automatic analyzer according to claim 1, further comprising:
a deterioration monitoring means for monitoring deterioration of the photomultiplier tube, where the deterioration monitoring means stores a cause of the deterioration of the photomultiplier tube, that is, at least one of a cumulative time of exposure of the photomultiplier tube to light, a cumulative number of measuring operations on the photomultiplier tube, and a cumulative number of maintenance operations thereon;

determination means for monitoring a rate of change of the gain to the cause of the deterioration and determining whether the gain stays within a predefined permissible range, and wherein, upon the determination means determining the gain to lie outside the permissible range, a warning is output.

6. The automatic analyzer according to claim 1,
wherein the determination means uses a reagent that the analyzer system uses on a routine basis as a reagent for measurement use in determining the value of the applied voltage.

7. The automatic analyzer according to claim 6, wherein the reagent used on a routine basis is a precision control sample or a standard solution.

8. The automatic analyzer according to claim 5, wherein the deterioration monitoring means is connected to a service center through a network; and information stored in the deterioration monitoring means is remotely collected at the service center.

9. The automatic analyzer according to claim 6, wherein the gain calculated by the calculating means, with respect to the reagent, is stored chronologically, and the warning means issues the warning if the gain stored in the means for storing oversteps the predefined threshold data range.

* * * * *